United States Patent
Mehrpouyan et al.

(10) Patent No.: US 9,863,947 B2
(45) Date of Patent: Jan. 9, 2018

(54) POLYMERSOME ENCAPSULATION OF HYDROPHOBIC FLUORESCENT POLYMERS

(71) Applicant: Becton, Dickinson and Company, Franklin Lakes, NJ (US)

(72) Inventors: Majid Mehrpouyan, Gilroy, CA (US); Shumeye Mamo, San Ramon, CA (US); Marybeth Sharkey, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/384,212

(22) Filed: Dec. 19, 2016

(65) Prior Publication Data

US 2017/0097348 A1 Apr. 6, 2017

Related U.S. Application Data

(63) Continuation of application No. 14/501,811, filed on Sep. 30, 2014.

(60) Provisional application No. 61/885,932, filed on Oct. 2, 2013.

(51) Int. Cl.
| | |
|---|---|
| A61K 9/00 | (2006.01) |
| G01N 33/566 | (2006.01) |
| C08J 3/05 | (2006.01) |
| C09K 11/06 | (2006.01) |
| C09K 11/02 | (2006.01) |
| B01J 13/08 | (2006.01) |
| G01N 21/64 | (2006.01) |

(52) U.S. Cl.
CPC ............ *G01N 33/566* (2013.01); *B01J 13/08* (2013.01); *C08J 3/05* (2013.01); *C09K 11/025* (2013.01); *C09K 11/06* (2013.01); *G01N 21/6428* (2013.01); *C08J 2365/00* (2013.01); *C08J 2367/04* (2013.01); *C09K 2211/14* (2013.01); *G01N 2021/6439* (2013.01); *G01N 2333/705* (2013.01)

(58) Field of Classification Search
CPC .................................................. G01N 33/566
See application file for complete search history.

(56) References Cited

U.S. PATENT DOCUMENTS

| | | | |
|---|---|---|---|
| 7,144,950 B2 | 12/2006 | Bazan et al. |
| 7,214,489 B2 | 5/2007 | Bazan et al. |
| 7,270,956 B2 | 9/2007 | Bazan et al. |
| 7,666,594 B2 | 2/2010 | Bazan et al. |
| 7,682,603 B2 | 3/2010 | Hammer et al. |
| 7,811,755 B2 | 10/2010 | Bazan et al. |

(Continued)

FOREIGN PATENT DOCUMENTS

WO  WO2009139856  11/2009

OTHER PUBLICATIONS

Alemdaroglu et al. "Poly(BODIPY)s: A New Class of Tunable Polymeric Dyes", Macromolecules, vol. 42, pp. 6529-6536 (2009).

(Continued)

*Primary Examiner* — Paul W Dickinson
(74) *Attorney, Agent, or Firm* — Glenn J. Foulds; Bret E. Field; Bozicevic, Field & Francis LLP

(57) ABSTRACT

Described herein are aqueous soluble polymersomes that encapsulate one or more hydrophobic fluorescent polymers and methods of their preparation and use.

21 Claims, 9 Drawing Sheets

(56) References Cited

U.S. PATENT DOCUMENTS

| | | | |
|---|---|---|---|
| 7,897,684 | B2 | 3/2011 | Bazan et al. |
| 8,158,444 | B2 | 4/2012 | Gaylord et al. |
| 8,575,303 | B2 | 11/2013 | Gaylord et al. |
| 8,969,509 | B2 | 3/2015 | Liu et al. |
| 8,993,335 | B2 | 3/2015 | Bazan et al. |
| 2008/0242806 | A1* | 10/2008 | Chen .......... C08J 3/03 525/450 |
| 2008/0293164 | A1 | 11/2008 | Gaylord et al. |
| 2009/0220614 | A1 | 9/2009 | Qin et al. |
| 2011/0223206 | A1 | 9/2011 | Lebouille et al. |
| 2012/0282632 | A1 | 11/2012 | Chiu et al. |
| 2013/0234067 | A1 | 9/2013 | Chiu et al. |

OTHER PUBLICATIONS

American Dye Source, Inc. Products Catalog, 2013, 38 pgs.
American Dye Source, Inc. Flourene Copolymers, Retrieved online Aug. 21, 2013, 3 pgs.
American Dye Source, Inc. Light Emitting Homopolymers, Retrieved online Aug. 21, 2013, 5 pgs.
Astete et al. "Synthesis and characterization of PLGA nanoparticles", J. Biomater. Sci. Polymer Edn, vol. 17, No. 3, pp. 247-289 (2006).
Christie et al. "Targeted Polymeric Micelles for siRNA Treatment of Experimental Cancer by Intravenous Injection", ACS Nano, 6(6): 5174-5189 (2012).
Cu et al. "Controlled Surface Modification with Poly(ethylene)glycol Enhances Diffusion of PLGA Nanoparticles in Human Cervical Mucus", Molecular Pharmaceutics, vol. 6, No. 1, pp. 173-181 (2009).
Evonik Industries AG. Resomer RG 502 H. Apr. 2013, 2 pgs., Retrieved from the Internet: http://www.resomer.com/producVbiodegradable-polymers/Documents/evonikspecification-resom er-rg-502-h. pdf.
Fischer et al. "Enhanced Brightness Emission-Tuned Nanoparticles from Heterodifunctional Polyfluorene Building Blocks", J. Am. Chem. Soc., vol. 135, pp. 1148-1154 (2013).
Hood et al. "Nanocarriers for vascular delivery of antioxidants", Nanomedicine 6(7):1257-1272 (Sep. 2011).
Nam et al. "New micelle-like polymer aggregates made from PEI-PLGA diblock copolymers: micellar characteristics and cellular uptake", Biomaterials 24, pp. 2053-2059 (2003).
Nehilla et al. "Surfactant-Free, Drug-Quantum-Dot Coloaded Poly(lactide-co-glycolide) Nanoparticles: Towards Multifunctional Nanoparticles", ACS Nano, vol. 2, No. 3, pp. 538-544 (2008).
Pecher et al. "Nanoparticles of Conjugated Polymers", Chem. Rev., vol. 110, No. 1 0, pp. 6260-6279 (2010).
Tian et al. "Conjugated Polymer Nanoparticles Incorporating Antifade Additives for Improved Brightness and Photostability", J. Phys. Chem. B, vol. 117, pp. 4517-4520 (2013).
Townsend et al. "Tetanus toxin C fragment-conjugated nanoparticles for targeted drug delivery to neurons", Biomaterials, vol. 28, No. 34, pp. 5176-5184 (2007).
Wagh et al. "Development of Biocompatible Polymeric Nanoparticles for in Vivo NIR and FRET Imaging", Bioconjugate Chem., vol. 23, No. 5, pp. 981-992 (2012).
Wu et al. "Energy Transfer in a Nanoscale Multichromophoric System: Fluorescent Dye-Doped Conjugated Polymer Nanoparticles", J. Phys. Chem. C, vol. 112, pp. 1772-1781(2008).

* cited by examiner

Left: PFbenzothiadiazole-encapsulated in PLGA-PEG polymersomes in $H_2O$

Right: PFbenzothiadiazole in $H_2O$

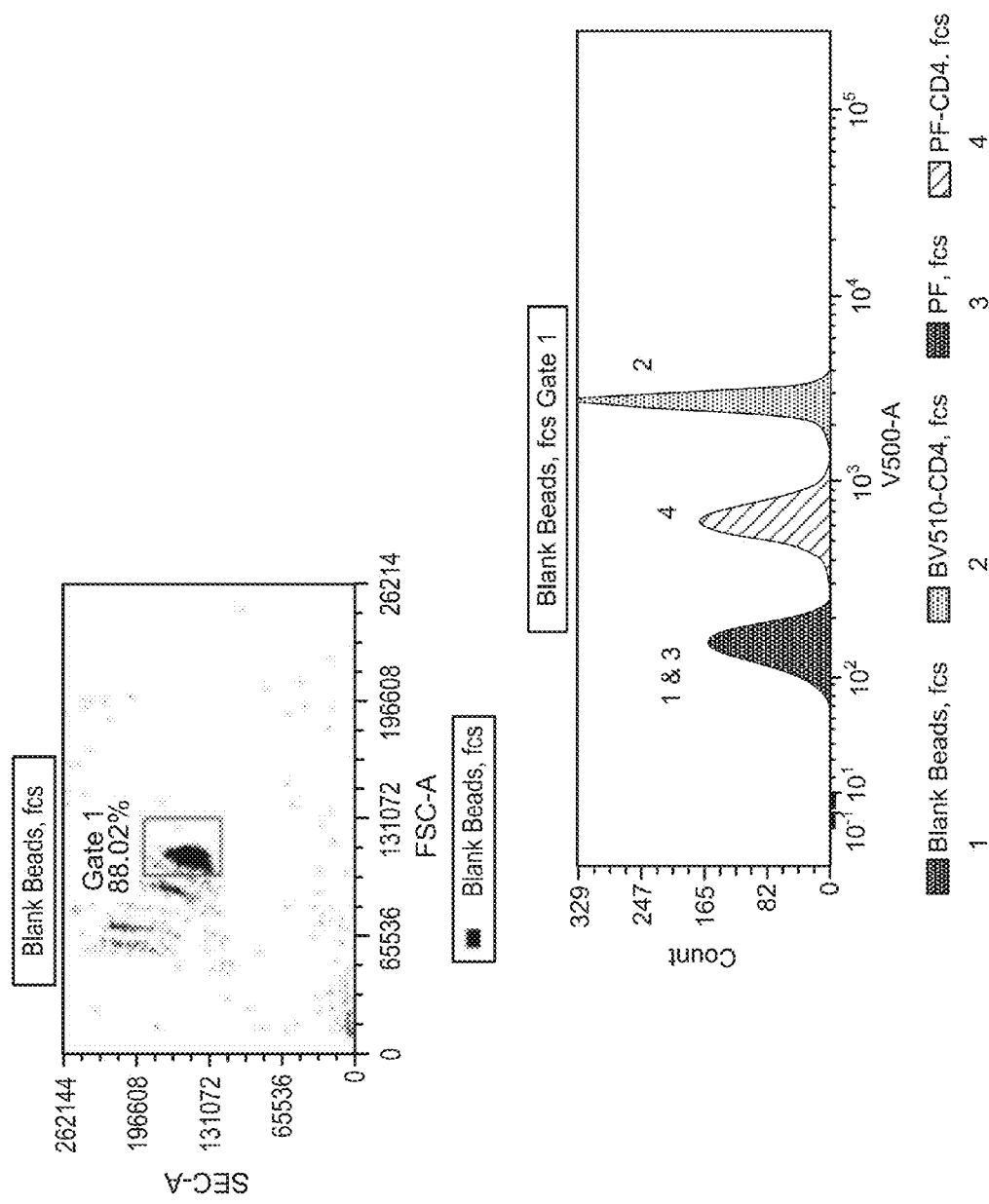

POLYMERSOME ENCAPSULATION OF HYDROPHOBIC FLUORESCENT POLYMERS

CROSS-REFERENCE TO RELATED APPLICATIONS

This application claims the benefit of U.S. Provisional Application No. 61/885,932, filed Oct. 2, 2013, which application is incorporated herein by reference in its entirety.

BACKGROUND OF THE INVENTION

Fluorescent polymers increasingly play an important role in the field of biochemistry, protein and cell studies. The signals generated by fluorescent polymers can be monitored in real time and provide simple, rapid, and robust methods for the detection of biological targets and events. Dye-labeled antibodies are regularly used for the detection of target biomolecules in applications such as immunohistochemistry, protein arrays, ELISA tests, and flow cytometry. Integrating fluorescent polymers into such methodologies promise to provide a dramatic boost in the performance of such assays, enabling detection levels previously unattainable with conventional dyes. In addition, multiple fluorescent polymers which operate at different, discernible wavelengths can be used simultaneously to detect multiple analytes in the same test or to multiplex.

SUMMARY OF THE INVENTION

In one aspect, provided herein are aqueous soluble polymersomes comprising: (a) one or more hydrophobic fluorescent polymers; and (b) a plurality of amphiphilic copolymers encapsulating the one or more hydrophobic fluorescent polymers, the copolymers each comprising a hydrophobic block that forms a hydrophobic core structure and a hydrophilic block on the surface of the polymersome that is oriented toward an aqueous phase.

In some embodiments described above or below of an aqueous soluble polymersome, the amphiphilic block copolymers are diblock copolymers that comprise one hydrophobic polymer block and one hydrophilic polymer block. In some embodiments, the amphiphilic block copolymers are triblock copolymers that comprise one hydrophobic polymer block and two hydrophilic polymer blocks. In other embodiments, the amphiphilic block copolymers are triblock copolymers that comprise two hydrophobic polymer blocks and one hydrophilic polymer block. In other embodiments, the amphiphilic block copolymers are tetrablock copolymers that comprise one hydrophobic polymer block and three hydrophilic polymer blocks, or two hydrophobic polymer blocks and two hydrophilic polymer blocks, or three hydrophobic polymer blocks and one hydrophilic polymer block. In other embodiments, the amphiphilic block copolymers are pentablock copolymers that comprise one hydrophobic polymer block and four hydrophilic polymer blocks, or two hydrophobic polymer blocks and three hydrophilic polymer blocks, or three hydrophobic polymer blocks and two hydrophilic polymer blocks, or four hydrophobic polymer blocks and one hydrophilic polymer block. In further embodiments, the amphiphilic block copolymers are hexablock copolymers that comprise of hydrophobic and hydrophilic polymer blocks that total six polymer blocks.

In some embodiments described above or below of an aqueous soluble polymersome, the hydrophobic block is selected from a polymer group consisting of polyacrylonitrile, polycarbonate, aromatic polyether, poly(vinyl acetal), poly(alkyl vinyl ether), poly(alkyl vinyl ketone), polyurethane, polyamide, polyimide, polyester, polyfluorocarbon, polyolefin, polystyrene, polyvinylcyclohexane, polydioxanone, polymeric organosilicon, polysaccharide, poly(methyl methacrylate), or a copolymer combination thereof.

In some embodiments described above or below of an aqueous soluble polymersome, the hydrophobic block is selected from a polymer group consisting of poly(lactide-co-glycolic acid (PLGA), polylactide (PLA), polyglycolide (PGA), polycaprolactone (PCL), poly(methyl methacylate) (PMMA), polydimethylsiloxane (PDMS), polyethylene (PE) and polystyrene (PS).

In some embodiments described above or below of an aqueous soluble polymersome, the hydrophobic block is poly(lactide-co-glycolic acid (PLGA).

In some embodiments described above or below of an aqueous soluble polymersome, the polymer ratio of PLGA is 50:50 (DL-lactide:glycolide).

In some embodiments described above or below of an aqueous soluble polymersome, the PLGA has a viscosity of about 0.15-0.25 dL/g.

In some embodiments described above or below of an aqueous soluble polymersome, the hydrophobic block has a number average molecular weight of about 2,000 to 20,000 Daltons. In some embodiments described above or below of an aqueous soluble polymersome, the hydrophobic block has a number average molecular weight of about 10,000 Daltons. In some embodiments described above or below of an aqueous soluble polymersome, the hydrophobic block has a number average molecular weight of about 5,000 Daltons.

In some embodiments described above or below of an aqueous soluble polymersome, the hydrophilic block is selected from a polymer group consisting of polyoxyalkylene, polymethacrylate, poly(methacrylic acid), polyacrylic acid, polyacrylate, poly(alkylacrylic acid), poly(alkylacrylate), polyacrylamide, poly(N-isopropylacrylamide), poly(2-ethyl-2-oxazoline), polyethylenimine, poly(vinyl alcohol), poly(vinylpyrrolidone), poly(styrenesulfonate), poly(vinyl acid), poly(allylamine), poly(diallyldimethyl ammonium chloride), poly(methyl vinyl ether), poly(2-methyloxazoline), or copolymer combinations thereof.

In some embodiments described above or below of an aqueous soluble polymersome, the hydrophilic block is polyether. In further embodiments described above or below of an aqueous soluble polymersome, the polyether is polypropylene glycol (PPG) or polyethylene glycol (PEG).

In some embodiments described above or below of an aqueous soluble polymersome, the hydrophilic block is poly(2-methyloxazoline).

In some embodiments described above or below of an aqueous soluble polymersome, the hydrophilic block has a number average molecular weight of about 1,000 to about 10,000 Daltons. In some embodiments described above or below of an aqueous soluble polymersome, the hydrophilic block has a number average molecular weight of about 5,000 Daltons. In some embodiments described above or below of an aqueous soluble polymersome, the hydrophilic block has a number average molecular weight of about 2,000 Daltons.

In some embodiments described above or below of an aqueous soluble polymersome, the hydrophilic block further comprises an amine moiety. In some embodiments described above or below of an aqueous soluble polymersome, the amine moiety is further thiolated with 2-iminothiolane (2-IT).

In some embodiments described above or below of an aqueous soluble polymersome, the hydrophilic block is attached to a biosensor molecule. In some embodiments described above or below of an aqueous soluble polymersome, the hydrophilic block is attached to a signaling chromophore for resonant energy transfer. In some embodiments described above or below of an aqueous soluble polymersome, the hydrophilic block is attached to an antigen-specific antibody.

In some embodiments described above or below of an aqueous soluble polymersome, the hydrophobic block is PLGA and the hydrophilic block is PEG. In some embodiments described above or below of an aqueous soluble polymersome, the PLGA has a number average molecular weight of about 5,000 Daltons and the PEG has a number average molecular weight of about 2,000 Daltons.

In some embodiments described above or below of an aqueous soluble polymersome, the one or more hydrophobic fluorescent polymers are polyfluorene polymer, polyfluorene copolymer, or fluorescent homopolymer.

In some embodiments described above or below of an aqueous soluble polymersome, the one or more hydrophobic fluorescent polymers are selected from poly[(9,9-dioctyl-2,7-divinylenefluorenylene)-alt-co-(9,10-anthracene)]; poly[(9,9-dioctyl-2,7-divinylenefluorenylene)-alt-co-{2-methoxy-5-(2-ethylhexyloxy)-1,4-phenylene}]; poly[(9,9-dioctyl-2,7-divinylenefluorenylene)-alt-co-(1,4-phenylene)]; poly[(9,9-dioctylfluorenyl-2,7-diyl)-alt-co-(1,4-benzo-{2,1',3}-thiadiazole)]; poly[(9,9-dihexylfluorenyl-2,7-diyl)-alt-co-(2-methoxy-5-{2-ethylhexyloxy}-1,4-phenylene)]; poly[(9,9-dioctylfluorenyl-2,7-diyl)-co-(2,5-p-xylene)]; poly[(9,9-dioctylfluorenyl-2,7-diyl)-co-(N,N'-diphenyl)-N,N'-di(p-butylphenyl)-1,4-diamino-benzene)]; poly[(9,9-dioctylfluorenyl-2,7-diyl)-co-(1,4-benzo-{2,1',3}-thiadiazole)]; poly[2-methoxy-5-(2-ethylhexyloxy)-1,4-phenylene-vinylene], optionally end capped with dimethylphenyl; poly[2-methoxy-5-(2-ethylhexyloxy)-1,4-phenylene-vinylene], optionally end capped with polysilsesquioxane; poly[2-methoxy-5-(3,7-dimethyloctyloxy)-1,4-phenylene-vinylene], optionally end capped with dimethylphenyl; poly[2-methoxy-5-(3,7-dimethyloctyloxy)-1,4-phenylene-vinylene], optionally end capped with polysilsesquioxane; poly[9,9-dioctylfluorenyl-2,7-diyl], optionally end capped with dimethylphenyl; poly[9,9-dioctylfluorenyl-2,7-diyl], optionally end capped with polysilsesquioxane; poly[9,9-dioctylfluorenyl-2,7-diyl], optionally end capped with N,N-bis(4-methylphenyl)-aniline; poly[9,9-dioctylfluorenyl-2,7-diyl], optionally end capped with 2,5-diphenyl-1,2,4-oxadiazole; poly[9,9-di-(2-ethylhexyl)-fluorenyl-2,7-diyl], optionally end capped with dimethylphenyl; poly[9,9-di-(2-ethylhexyl)-fluorenyl-2,7-diyl], optionally end capped with polysilsesquioxane; poly[9,9-di-(2-ethylhexyl)-fluorenyl-2,7-diyl], optionally end capped with N,N-bis(4-methylphenyl)-aniline; poly[9,9-di-(2-ethylhexyl)-fluorenyl-2,7-diyl], optionally end capped with 2,5-diphenyl-1,2,4-oxadiazole; poly[2-(5-cyano-5-methylhexyloxy)-1,4-phenylene], optionally end capped with dimethylphenyl; and poly[2,5-dioctyl-1,4-phenylene], optionally end capped with dimethylphenyl; poly[9,9-di(3,3'-N,N'-trimethyl-ammonium)propylfluorenyl-2,7-diyl]-alt-(9,9-dioctylfluorenyl-2,7-diyl)] diiodide salt, optionally end capped with dimethylphenyl; poly[2,5-bis(3,7-dimethyloctyloxy)-1,4-phenylene-vinylene]; poly(9,9-di{2-[2-(2-methoxy-ethoxy)ethoxy]ethyl}fluorenyl-2,7-diyl), optionally end capped with dimethylphenyl; and poly-BODIPY fluorescent polymers.

In some embodiments described above or below of an aqueous soluble polymersome, the one or more hydrophobic fluorescent polymers are selected from the optionally substituted polymer group consisting of poly(fluorene), poly(fluorene-alt-benzothiadiazole), poly(fluorene-alt-benzooxadiazole), poly(fluorene-alt-thiophene), and poly(fluorene-alt-phenylene).

In some embodiments described above or below of an aqueous soluble polymersome, the hydrophobic fluorescent polymer is optionally substituted poly(fluorene-alt-benzothiadiazole).

In some embodiments described above or below of an aqueous soluble polymersome, the polymersome comprises at least two hydrophobic fluorescent polymers. In some embodiments described above or below of an aqueous soluble polymersome, at least one hydrophobic fluorescent polymer acts as a light harvesting polymer and at least one hydrophobic fluorescent polymer acts as a signaling chromophore in a FRET process.

In some embodiments described above or below of an aqueous soluble polymersome, each of the one or more hydrophobic fluorescent polymers has a number average molecular weight of about 5,000 to about 30,000 Daltons. In some embodiments described above or below of an aqueous soluble polymersome, each of the one or more hydrophobic fluorescent polymers has a number average molecular weight of about 10,000 to about 20,000 Daltons.

In some embodiments described above or below of an aqueous soluble polymersome, the polymersome has an average particle size of about 200 nm. In some embodiments described above or below of an aqueous soluble polymersome, the polymersome has an average particle size of about 100 nm.

In some embodiments described above or below of an aqueous soluble polymersome, the polymersome further comprises one or more antioxidants. In some embodiments described above or below of an aqueous soluble polymersome, the one or more antioxidants are selected from butylated hydroxytoluene (BHT), 3-(3,5-ditert-butyl-4-hydroxyphenyl) propionic acid stearyl ester (PASE), triphenylamine (TPA), trans-stilbene (TSB), cyclooctatetraene (Cot), 4-nitrobenzyl alcohol (NBA), and 6-hydroxy-2,5,7,8-tetramethylchroman-2-carboxylic acid (Trolox).

In another aspect, provided herein are aqueous soluble polymersomes comprising: (a) one or more hydrophobic fluorescent polymers; and (b) a plurality of amphiphilic diblock copolymers encapsulating the one or more hydrophobic fluorescent polymers, the diblock copolymers each having a hydrophobic block that forms a hydrophobic core structure and a hydrophilic block on the surface of the polymersome that is oriented toward an aqueous phase.

In another aspect, provided herein are methods of preparing an aqueous soluble polymersome comprising one or more hydrophobic fluorescent polymers, the method comprising: (a) forming a plurality of amphiphilic copolymers each comprising a hydrophobic block and a hydrophilic block; (b) adding one or more hydrophobic fluorescent polymers to the plurality of amphiphilic copolymers; and (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of the polymersome that is oriented toward an aqueous phase.

In some embodiments described above or below of a method of preparing an aqueous soluble polymersome, the amphiphilic block copolymers are diblock copolymers that comprise one hydrophobic polymer block and one hydrophilic polymer block. In some embodiments, the amphiphilic block copolymers are triblock copolymers that comprise one hydrophobic polymer block and two hydrophilic polymer blocks. In other embodiments, the amphiphilic block copolymers are triblock copolymers that comprise two hydrophobic polymer blocks and one hydrophilic polymer block. In other embodiments, the amphiphilic block copolymers are tetrablock copolymers that comprise one hydrophobic polymer block and three hydrophilic polymer blocks, or two hydrophobic polymer blocks and two hydrophilic polymer blocks, or three hydrophobic polymer blocks and one hydrophilic polymer block. In other embodiments, the amphiphilic block copolymers are pentablock copolymers that comprise one hydrophobic polymer block and four hydrophilic polymer blocks, or two hydrophobic polymer blocks and three hydrophilic polymer blocks, or three hydrophobic polymer blocks and two hydrophilic polymer blocks, or four hydrophobic polymer blocks and one hydrophilic polymer block. In further embodiments, the amphiphilic block copolymers are hexablock copolymers that comprise of hydrophobic and hydrophilic polymer blocks that total six polymer blocks.

In some embodiments described above or below of a method of preparing an aqueous soluble polymersome, the hydrophobic block of plurality of amphiphilic copolymers is PLGA.

In some embodiments described above or below of a method of preparing an aqueous soluble polymersome, the hydrophilic block of plurality of amphiphilic copolymers is PEG.

In some embodiments described above or below of a method of preparing an aqueous soluble polymersome, the formation of the amphiphilic copolymers comprises reacting PLGA with bis-aminopropyl-PEG in the presence of carbodiimide.

In some embodiments described above or below of a method of preparing an aqueous soluble polymersome, in step (c), the mixture and aqueous system is agitated. In some embodiments described above or below of a method of preparing an aqueous soluble polymersome, in step (c), the mixture and aqueous system is agitated by vigorous stirring. In other embodiments described above or below of a method of preparing an aqueous soluble polymersome, in step (c), the mixture and aqueous system is agitated by ultra-sonication.

In some embodiments described above or below of a method of preparing an aqueous soluble polymersome, the method further comprises filtering the polymersomes in the aqueous system.

In some embodiments described above or below of a method of preparing an aqueous soluble polymersome, the method further comprises concentrating the polymersomes in the aqueous system.

In some embodiments described above or below of a method of preparing an aqueous soluble polymersome, the method further comprises reacting the polymersomes with a thiolating reagent.

In some embodiments described above or below of a method of preparing an aqueous soluble polymersome, the method further comprises attaching an antigen-specific antibody to the polymersomes.

In another aspect, provided herein are methods of preparing an aqueous soluble polymersome comprising one or more hydrophobic fluorescent polymers, the method comprising: (a) forming a plurality of amphiphilic diblock copolymers each having a hydrophobic block and a hydrophilic block; (b) adding one or more hydrophobic fluorescent polymers to the plurality of amphiphilic diblock copolymers; and (c) placing the mixture of step (b) into an aqueous system so that the plurality of amphiphilic diblock copolymers encapsulate the one or more hydrophobic fluorescent polymers, wherein the hydrophobic block forms a hydrophobic core structure and a hydrophilic block is oriented on the surface of the polymersome that is oriented toward an aqueous phase.

In another aspect, provided herein are methods of solubilizing one or more hydrophobic fluorescent polymers, the method comprising: (a) forming a plurality of amphiphilic copolymers each comprising a hydrophobic block and a hydrophilic block; (b) adding one or more hydrophobic fluorescent polymers to the plurality of amphiphilic copolymers; and (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of the polymersome that is oriented toward an aqueous phase.

In some embodiments described above or below of methods of solubilizing one or more hydrophobic fluorescent polymers, the amphiphilic block copolymers are diblock copolymers that comprise one hydrophobic polymer block and one hydrophilic polymer block. In some embodiments, the amphiphilic block copolymers are triblock copolymers that comprise one hydrophobic polymer block and two hydrophilic polymer blocks. In other embodiments, the amphiphilic block copolymers are triblock copolymers that comprise two hydrophobic polymer blocks and one hydrophilic polymer block. In other embodiments, the amphiphilic block copolymers are tetrablock copolymers that comprise one hydrophobic polymer block and three hydrophilic polymer blocks, or two hydrophobic polymer blocks and two hydrophilic polymer blocks, or three hydrophobic polymer blocks and one hydrophilic polymer block. In other embodiments, the amphiphilic block copolymers are pentablock copolymers that comprise one hydrophobic polymer block and four hydrophilic polymer blocks, or two hydrophobic polymer blocks and three hydrophilic polymer blocks, or three hydrophobic polymer blocks and two hydrophilic polymer blocks, or four hydrophobic polymer blocks and one hydrophilic polymer block. In further embodiments, the amphiphilic block copolymers are hexablock copolymers that comprise of hydrophobic and hydrophilic polymer blocks that total six polymer blocks.

In another aspect, provided herein are methods of solubilizing one or more hydrophobic fluorescent polymers, the method comprising: (a) forming a plurality of amphiphilic diblock copolymers each having a hydrophobic block and a hydrophilic block; (b) adding one or more hydrophobic fluorescent polymers to the plurality of amphiphilic diblock copolymers; and (c) placing the mixture of step (b) into an aqueous system so that the plurality of amphiphilic diblock copolymers encapsulate the one or more hydrophobic fluorescent polymers, wherein the hydrophobic block forms a hydrophobic core structure and a hydrophilic block is oriented on the surface of the polymersome that is oriented toward an aqueous phase.

In another aspect, provided herein are assay methods for detecting a target biomolecule in a sample comprising: (a) providing a sample that is suspected of containing a target biomolecule; (b) providing an aqueous soluble polymersome of claim 1 that is conjugated to a sensor biomolecule, wherein the sensor biomolecule is capable of interacting with the target biomolecule or a target-associated biomolecule and wherein the polymersome optionally comprises an acceptor dye; (c) contacting the sample with the sensor biomolecule and the aqueous soluble polymersome in a solution under conditions in which the sensor biomolecule can bind to the target biomolecule or a target-associated biomolecule if present; and (d) applying a light source to the sample that can excite the fluorescent polyfluorene polymer in the polymersome, and detecting whether light is emitted from the polymersome.

In some embodiments described above or below of an assay method, the sensor biomolecule is a protein, peptide, affinity ligand, antibody, antibody fragment, sugar, lipid, nucleic acid or an aptamer.

In some embodiments described above or below of an assay method, the sensor biomolecule is an antibody.

In some embodiments described above or below of an assay method, the target biomolecule is a target protein expressed on a cell surface.

In some embodiments described above or below of an assay method, the method is configured for flow cytometry, intracellular staining, immunohistochemistry or FISH.

In another aspect, provided herein are aqueous soluble polymersomes comprising: (a) one or more hydrophobic fluorescent polymers; (b) a plurality of amphiphilic copolymers encapsulating the one or more hydrophobic fluorescent polymers, the copolymers each comprising a hydrophobic block that forms a hydrophobic core structure and a hydrophilic block on the surface of the polymersome that is oriented toward an aqueous phase; and (c) an acceptor dye.

In another aspect, provided herein are aqueous soluble polymersomes comprising: (a) one or more hydrophobic fluorescent polymers; (b) a plurality of amphiphilic copolymers encapsulating the one or more hydrophobic fluorescent polymers, the copolymers each comprising a hydrophobic block that forms a hydrophobic core structure and a hydrophilic block on the surface of the polymersome that is oriented toward an aqueous phase; (c) an acceptor dye; and (d) one or more antioxidants.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF FIGURES

FIG. 9 illustrates the flow cytometric analysis of the fluorescent antibody-polymersome conjugates of FIG. 7 after being captured on anti-kappa beads; in this case, "1" designates the signal from blank beads, "2" designates the signal from BV510-CD4 conjugate, "3" designates the signal from the unmodified fluorescent polymersomes of FIG. 1, and "4" designates the signal from the fluorescent antibody-polymersome conjugates of FIG. 7.

DETAILED DESCRIPTION OF THE INVENTION

Figure 1:
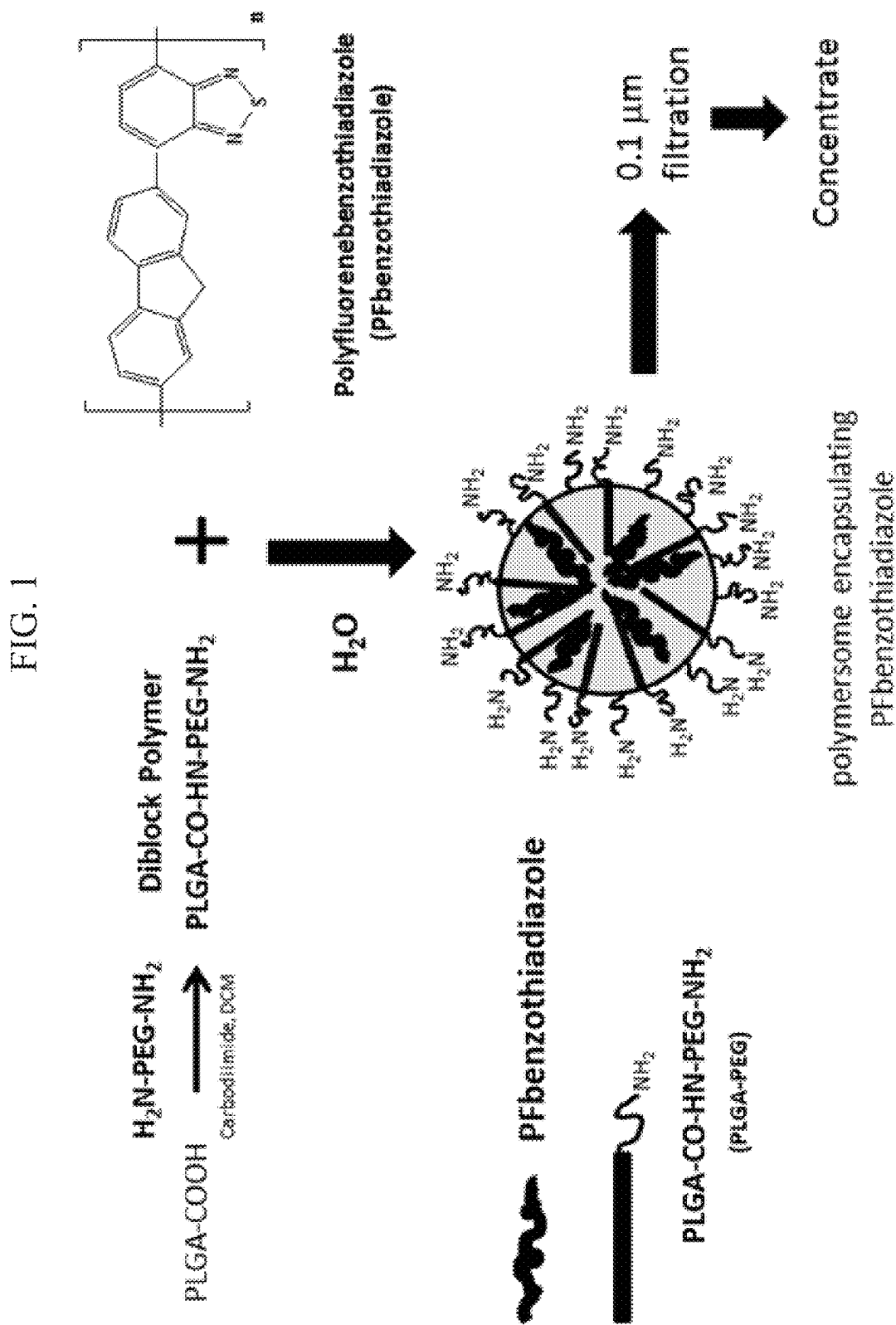
FIG. 1 illustrates a general scheme for the preparation of a non-limiting example of hydrophobic fluorescent polymer (polyfluorenebenzothiadiazole) encapsulated in aqueous soluble polymersomes, in which the carrier polymer is PLGA-CO—NH-PEG-NH$_2$.

Provided here are water-soluble polymersomes that encapsulate water-insoluble, highly fluorescent polymers and methods of their preparation and use. The polymersomes described herein are useful as part of biological sensors in detecting target biomolecules in a system.

Disclosed herein, in certain embodiments, are aqueous soluble polymersomes comprising a hydrophobic fluorescent polymer and a plurality of amphiphilic copolymers encapsulating the fluorescent polyfluorene polymer, the copolymers each comprising a hydrophobic block that forms a hydrophobic core structure and a hydrophilic block on the surface of the polymersome that is oriented toward an aqueous phase. In some embodiments, the polymersomes self-assemble from amphiphilic block copolymers in the presence of one or more hydrophobic fluorescent polymers. In other embodiments, the polymersomes self-assemble from amphiphilic block copolymers in the presence of one or more hydrophobic fluorescent polymers and one or more hydrophobic antioxidants.

The amphiphilic block copolymers comprise at least one hydrophobic polymer block and at least one hydrophilic polymer block. Due to the hydrophobic nature of the fluorescent polymer(s), the antioxidant(s), and the hydrophobic polymer blocks, these polymers self-assemble together into a hydrophobic core structure, encapsulating the fluorescent polymer(s) and the antioxidant(s), when the amphiphilic block copolymers, the fluorescent polymer(s), and the antioxidant(s) are vigorously mixed together in the presence of water. The hydrophilic polymer blocks orient themselves towards the surface of the polymersome, thereby solubilizing the whole polymersome in an aqueous system.

In some embodiments, the hydrophilic polymer block further comprises a reactive chemical moiety for covalent attachment of an antigen-specific antibody to form an antibody-polymersome conjugate. In some embodiments, the antibody-polymersome conjugate is used as a specific labeling agent for cell staining, either for cell surface or intercellular markers. In other embodiments, the antibody-polymersome conjugate is used for the detection of analytes in a cell-free assay system.

Polymersomes

Polymersomes, as disclosed herein, are enclosures, self-assembled from amphiphilic block copolymers. These amphiphilic block copolymers are macromolecules comprising at least one hydrophobic polymer block and at least one hydrophilic polymer block. When hydrated, these amphiphilic block copolymers self-assemble into enclosures such that the hydrophobic blocks tend to associate with each other to minimize direct exposure to water and form the inner surface of the enclosure, and the hydrophilic blocks face outward, forming the outer surface of the enclosure. The hydrophobic core of these aqueous soluble polymersomes may provide an environment to solubilize additional hydrophobic molecules. As such, these aqueous soluble polymersomes may act as carrier polymers for hydrophobic molecules encapsulated within the polymersomes. Moreover, the self-assembly of the amphiphilic block polymers occurs in the absence of stabilizers, which would otherwise provide colloidal stability and prevent aggregation.

In some embodiments, these aqueous soluble polymersomes encapsulate one or more hydrophobic fluorescent polymers when the self-assembly occurs in the presence of one or more fluorescent polymers. In some embodiments, these aqueous soluble polymersomes encapsulate one or more hydrophobic fluorescent polymers and an acceptor dye when the self-assembly occurs in the presence of one or more fluorescent polymers and an acceptor dye. In other embodiments, these aqueous soluble polymersomes further comprise one or more hydrophobic antioxidants when the self-assembly occurs in the presence of one or more antioxidants. In some embodiments, the aqueous soluble polymersomes are self-assembled prior to the encapsulation of one or more fluorescent polymers. In some embodiments, the aqueous soluble polymersomes are self-assembled prior to the encapsulation of one or more fluorescent polymers and an acceptor dye. In other embodiments, the aqueous soluble polymersomes are self-assembled prior to the encapsulation of one or more fluorescent polymers and one or more antioxidants. In some embodiments, the aqueous soluble polymersomes are self-assembled prior to the encapsulation of one or more fluorescent polymers, an acceptor dye, and one or more antioxidants. In other embodiments, the aqueous soluble polymersomes are self-assembled prior to the encapsulation of one or more fluorescent polymers, an acceptor dye, and one or more antioxidants. In some embodiments, the aqueous soluble polymersomes are self-assembled in the presence of one or more fluorescent polymers prior to the addition of one or more antioxidants. In some embodiments, the aqueous soluble polymersomes are self-assembled in the presence of one or more fluorescent polymers and an acceptor dye prior to the addition of one or more antioxidants. In other embodiments, the aqueous soluble polymersomes are self-assembled in the presence of one or more antioxidants prior to the addition of one or more fluorescent polymers.

In some embodiments, the one or more hydrophobic fluorescent polymers are polyfluorene polymers, polyfluorene copolymers, or fluorescent homopolymers. In some embodiments, the hydrophobic fluorescent polymers are devoid of any reactive functional groups. These hydrophobic fluorescent polymers may be used without further modification to generate fluorescently labeled water-soluble polymersomes, once the hydrophobic fluorescent polymers are encapsulated within the polymersome. These hydrophobic fluorescent polymers are not covalently attached to the carrier polymer (i.e., aqueous soluble polymersome).

In some embodiments, the aqueous soluble polymersome encapsulates at least one hydrophobic fluorescent polymer that acts as a light harvesting system (donor dye) and at least one acceptor dye that acts as the signaling chromophore in a FRET process. In some embodiments, the acceptor dye is a hydrophobic fluorescent polymer.

In some embodiments, the amphiphilic block copolymers are diblock copolymers that comprise one hydrophobic polymer block and one hydrophilic polymer block. In some embodiments, the amphiphilic block copolymers are triblock copolymers that comprise one hydrophobic polymer block and two hydrophilic polymer blocks. In other embodiments, the amphiphilic block copolymers are triblock copolymers that comprise two hydrophobic polymer blocks and one hydrophilic polymer block. In other embodiments, the amphiphilic block copolymers are tetrablock copolymers that comprise one hydrophobic polymer block and three hydrophilic polymer blocks, or two hydrophobic polymer blocks and two hydrophilic polymer blocks, or three hydrophobic polymer blocks and one hydrophilic polymer block. In other embodiments, the amphiphilic block copolymers are pentablock copolymers that comprise one hydrophobic polymer block and four hydrophilic polymer blocks, or two hydrophobic polymer blocks and three hydrophilic polymer blocks, or three hydrophobic polymer blocks and two hydrophilic polymer blocks, or four hydrophobic polymer blocks and one hydrophilic polymer block. In further embodiments, the amphiphilic block copolymers are hexablock copolymers that comprise of hydrophobic and hydrophilic polymer blocks that total six polymer blocks.

In some embodiments, the ratio of the hydrophobic polymer block to the hydrophilic polymer block is 20:80, 25:75, 30:70, 35:65, 40:60, 45:55, 50:50, 55:45, 60:40, 65:35, 70:30, 75:25, 80:20, or any ratio in between. In some embodiments, the ratio of the hydrophobic polymer block to the hydrophilic polymer block is 20:80 to 80:20. In some embodiments, the ratio of the hydrophobic polymer block to the hydrophilic polymer block is 30:70 to 70:30. In some embodiments, the ratio of the hydrophobic polymer block to the hydrophilic polymer block is 40:60 to 60:40.

The polymer blocks include, but are not limited to, polyglycolides (PGA), polylactides (LPLA and DPLA), polycaprolactone, polydioxanone (PDO or PDS), poly(lactide-co-glycolide) (PLGA), polyanhydrides, polyorthoesters, poly(amino acids) and "pseudo"-poly(amino acids), polyhydroxybutyrate (PHB), polyhydroxyvalerate (PHV), polycyanoacrylates, polyphosphazenes, polyphophonates, polyiminocarbonates, polyamines, polyolefins, polystyrene, polyoxyalkylene, thermoset amino proteins, polysaccharides, poly(methyl methacrylate) (PMMA), polytetrafluoroethylene (PTFE), polyurethane, polyvinylchloride (PVC), polydimethylsiloxane (PDMS), polyesters, nylons, lignin-based biodegradable polymers, biodegradable polymers from soybeans, soy protein-based plastics, loose fill from corn, polymers based on synthetic genes, bacterially-produced polymers such as polyhydroxyalkanoates, and copolymer combinations thereof.

The hydrophilic block of the polymersome may be poly(lactic-co-glycolic acid) (PLGA), and the hydrophilic block of the polymersome may be polyethylene glycol (PEG). The PLGA may have a number average molecular weight of about 5,000 Daltons and the PEG may have a number average molecular weight of about 2,000 Daltons.

In various embodiments, the polymersome has an average particle size of about, for example, 25, 50, 100, 200, 300, 400, 500, 600, 700, 800, 900, 1000, 2000, 3000, 4000, 5000, 6000, 7000, 8000, 9000, 10000, 11000, 12000, 13000, 14000, 15000, 16000, 17000, 18000, 20000 nm or more, including increments therein. In some embodiments, the polymersome has an average particle size of about 100 nm. In some embodiments, the polymersome has an average particle size of about 200 nm. In some embodiments, the polymersome has an average particle size of about 300 nm. In some embodiments, the polymersome has an average particle size of about 400 nm. In some embodiments, the polymersome has an average particle size of about 500 nm. In some embodiments, the polymersome has an average particle size of about 600 nm. In some embodiments, the polymersome has an average particle size of about 700 nm. In some embodiments, the polymersome has an average particle size of about 800 nm. In some embodiments, the polymersome has an average particle size of about 900 nm. In some embodiments, the polymersome has an average particle size of about 1000 nm. In some embodiments, the polymersome has an average particle size of about 100-300 nm. In some embodiments, the polymersome has an average particle size of about 100-400 nm. In some embodiments, the polymersome has an average particle size of about 100-500 nm. In some embodiments, the polymersome has an average particle size of about 100-600 nm. In some embodiments, the polymersome has an average particle size of about 200-500 nm. In some embodiments, the polymersome has an average particle size of about 200-600 nm. In some embodiments, the polymersome has an average particle size of about 200-700 nm. In some embodiments, the polymersome has an average particle size of about 100-1000 nm. In some embodiments, the polymersome has an average particle size of about 25-100 nm. In some embodiments, the polymersome has an average particle size of about 25-200 nm. In some embodiments, the polymersome is considered to be a nanoparticle.

Hydrophobic Polymer Block

Hydrophobic polymer blocks are insoluble in water. In various embodiments, the hydrophobic polymer blocks have a number average molecular weight of about 1000, 2000, 3000, 4000, 5000, 6000, 7000, 8000, 9000, 10000, 11000, 12000, 13000, 14000, 15000, 16000, 17000, 18000, 19000, or 20000 Daltons, including increments therein. In some embodiments, the hydrophobic polymer blocks have a number average molecular weight of about 2,000 to 20,000 Daltons. In some embodiments, the hydrophobic polymer blocks have a number average molecular weight of about 2,000 to 5,000 Daltons. In some embodiments, the hydrophobic polymer blocks have a number average molecular weight of about 2,000 to 8,000 Daltons. In some embodiments, the hydrophobic polymer blocks have a number average molecular weight of about 2,000 to 10,000 Daltons. In some embodiments, the hydrophobic polymer blocks have a number average molecular weight of about 2,000 to 15,000 Daltons. In some embodiments, the hydrophobic polymer blocks have a number average molecular weight of about 5,000 to 10,000 Daltons. In some embodiments, the hydrophobic polymer blocks have a number average molecular weight of about 5,000 to 15,000 Daltons. In some embodiments, the hydrophobic polymer blocks have a number average molecular weight of about 10,000 Daltons. In some embodiments, the hydrophobic polymer blocks have a number average molecular weight of about 5,000 Daltons.

In some embodiments, the hydrophobic polymer block is polyacrylonitrile, polycarbonate, aromatic polyether, poly(vinyl acetal), poly(alkyl vinyl ether), poly(alkyl vinyl ketone), polyurethane, polyamide, polyimide, polyester, polyfluorocarbon, polyolefin, polystyrene, polyvinylcyclohexane, polydioxanone, polymeric organosilicon, polysaccharide, poly(methyl methacrylate), or a copolymer combination thereof. In some embodiments, the hydrophobic polymer block is poly(lactic-co-glycolic acid) (PLGA). In some embodiments, the PLGA has a viscosity of about 0.15-0.25 dL/g.

In some embodiments, the hydrophobic polymer block is a polyamide. In some embodiments, the polyamide is an aliphatic polyamide. In some embodiments, the hydrophobic polymer block is a polyimide. In some embodiments, the polyimide is polyetherimide, polymaleimide, or a copolymer combination thereof.

In some embodiments, the hydrophobic polymer block is a polyester. In some embodiments, the polyester is unsaturated or saturated. In some embodiments, the polyester is a polyhydroxyalkanoate. In some embodiments, the polyester is polylactide, a polyglycolide, polycaprolactone, poly-3-hydroxybutyrate, poly-4-hydroxybutyrate a polyhydroxyvalerate, poly-hydroxyhexanoate, poly-hydroxyoctanoate, or a copolymer combination thereof.

In some embodiments, the hydrophobic polymer block is a polyfluorocarbon. In some embodiments, the polyfluorocarbon is polytetrafluoroethylene, poly(vinylidene fluoride), poly(chlorotrifluoroethylene), or a copolymer combination thereof.

In some embodiments, the hydrophobic polymer block is a polyolefin. In some embodiments, the polyolefin is polyethylene, polypropylene, polybutene, polyisobutylene, poly(4-methyl-1-pentene), or a copolymer combination thereof.

In some embodiments, the hydrophobic polymer block is a polystyrene. In some embodiments, the polystyrene is substituted or unsubstituted. In some embodiments, the hydrophobic polymer block is polyvinylcyclohexane.

In some embodiments, the hydrophobic polymer block is a polymeric organosilicon. In some embodiments, the polymeric organosilicon is polydimethylsiloxane.

In some embodiments, the hydrophobic polymer block is a hydrophobic polysaccharide. In some embodiments, the polysaccharide is a cellulosic polymer.

In some embodiments, the hydrophobic polymer block is polyacrylonitrile. In some embodiments, the hydrophobic polymer block is polycarbonate. In some embodiments, the hydrophobic polymer block is aromatic polyether. In some embodiments, the hydrophobic polymer block is poly(vinyl acetal). In some embodiments, the hydrophobic polymer block is poly(alkyl vinyl ether). In some embodiments, the hydrophobic polymer block is poly(alkyl vinyl ketone). In some embodiments, the hydrophobic polymer block is polyurethane. In some embodiments, the hydrophobic polymer block is polydioxanone. In some embodiments, the hydrophobic polymer block is polycyanoacrylate. In some embodiments, the hydrophobic polymer block is poly(methyl methacrylate).

In some embodiments, the hydrophobic polymer block is selected from a polymer group consisting of poly(lactide-co-glycolic acid (PLGA), polylactide (PLA), polyglycolide (PGA), polycaprolactone (PCL), poly(methyl methacylate) (PMMA), polydimethylsiloxane (PDMS), polyethylene (PE) and polystyrene (PS).

In various embodiments, the ratio of two copolymers in the hydrophobic polymer block is 20:80, 25:75, 30:70, 35:65, 40:60, 45:55, 50:50, 55:45, 60:40, 65:35, 70:30, 75:25, 80:20, 85:15 or any ratio in between. In some embodiments, the ratio of two copolymers in the hydrophobic polymer block is 20:80 to 80:20. In some embodiments, the ratio of two copolymers in the hydrophobic polymer block is 30:70 to 70:30. In some embodiments, the ratio of two copolymers in the hydrophobic polymer block is 40:60 to 60:40. In some embodiments, the ratio of two copolymers in the hydrophobic polymer block is 50:50 to 85:15.

Hydrophilic Polymer Block

Hydrophilic polymer blocks contain polar or charged functional groups, rendering them soluble in water. In various embodiments, the hydrophilic polymer blocks have a number average molecular weight of about 1000, 2000, 3000, 4000, 5000, 6000, 7000, 8000, 9000, 10000, 11000, 12000, 13000, 14000, 15000, 16000, 17000, 18000, 19000, or 20000 Daltons, including increments therein. In some embodiments, the hydrophilic polymer block has a number average molecular weight of about 1,000 to about 2,000 Daltons. In some embodiments, the hydrophilic polymer block has a number average molecular weight of about 1,000 to about 3,000 Daltons. In some embodiments, the hydrophilic polymer block has a number average molecular weight of about 1,000 to about 5,000 Daltons. In some embodiments, the hydrophilic polymer block has a number average molecular weight of about 1,000 to about 8,000 Daltons. In some embodiments, the hydrophilic polymer block has a number average molecular weight of about 1,000 to about 10,000 Daltons. In some embodiments, the hydrophilic polymer block has a number average molecular weight of about 2,000 to about 5,000 Daltons. In some embodiments, the hydrophilic polymer block has a number average molecular weight of about 2,000 to about 8,000 Daltons. In some embodiments, the hydrophilic polymer block has a number average molecular weight of about 5,000 to about 15,000 Daltons. In some embodiments, the hydrophilic polymer block has a number average molecular weight of about 2,000 to about 20,000 Daltons. In some embodiments, the hydrophilic polymer blocks have a number average molecular weight of about 5,000 Daltons. In some embodiments, the hydrophilic polymer blocks have a number average molecular weight of about 2,000 Daltons.

In some embodiments, the hydrophilic polymer block is polyoxyalkylene, polymethacrylate, poly(methacrylic acid), polyacrylic acid, polyacrylate, poly(alkylacrylic acid), poly(alkylacrylate), polyacrylamide, poly(N-isopropylacrylamide), poly(2-ethyl-2-oxazoline), polyethylenimine, poly(vinyl alcohol), poly(vinylpyrrolidone), poly(styrenesulfonate), poly(vinyl acid), poly(allylamine), poly(diallyldimethyl ammonium chloride), poly(methyl vinyl ether), poly(2-methyloxazoline), or copolymer combinations thereof.

In some embodiments, the hydrophilic polymer block is a polyether. In some embodiments, the polyether is a polyoxyalkylene polymer. In some embodiments, the polyoxyalkylene polymer is polyoxyethylene (or polyethylene glycol), polyoxypropylene (polypropylene glycol), polyoxybutylene, or copolymer combinations thereof. In some embodiments, the hydrophilic polymer block is derived from units of one or more alkyl oxide monomers. In some embodiments, the one or more alkyl oxide monomers are ethylene oxide, propylene oxide, or copolymer combinations thereof. In some embodiments, the hydrophilic polymer block is derived from units of one or more alkylene glycol monomers. In some embodiments, the one or more alkylene glycol monomers are ethylene glycol, polypropylene glycol, or combinations thereof.

In some embodiments, the hydrophilic polymer block is polymethacrylate salt, poly(methacrylic acid), derivatives of poly(methacrylic acid) or copolymer combinations thereof.

In some embodiments, the hydrophilic polymer block is polyacrylic acid, polyacrylate salt, a derivative of polyacrylic acid, or copolymer combinations thereof. In some embodiments, the hydrophilic polymer block may be poly(alkylacrylic acid), poly(alkylacrylate) salt, a derivative of poly(alkylacrylic acid), or copolymer combinations thereof.

In some embodiments, the hydrophilic polymer block may be polyacrylamide (PAM). In some embodiments, the hydrophilic polymer block may be poly(N-isopropylacrylamide) (PNIPAM).

In some embodiments, the hydrophilic polymer block is a hydrophilic polysaccharide. In some embodiments, the polysaccharide may be dextrin or amylopectin. In some embodiments, the polysaccharide may be dextrin. In other embodiments, the polysaccharide may be amylopectin.

In some embodiments, the hydrophilic polymer block is poly(2-ethyl-2-oxazoline). In some embodiments, the hydrophilic polymer block is polyethylenimine (PEI). In some embodiments, the hydrophilic polymer block is poly(vinyl alcohol) (PVA). In some embodiments, the hydrophilic polymer block is poly(vinylpyrrolidone) (PVP). In some embodiments, the hydrophilic polymer block is poly(styrenesulfonate) (PSS). In some embodiments, the hydrophilic polymer block is poly(vinyl acid) or their associated salts. The poly(vinyl acid) may be poly(vinylphosphonic acid), poly(vinyl sulfonic acid), their associated salts, or copolymer combinations thereof. In some embodiments, the hydrophilic polymer block is poly(allylamine). In some embodiments, the hydrophilic polymer block is poly(diallyldimethyl ammonium chloride). In some embodiments, the hydrophilic polymer block is poly(methyl vinyl ether). In some embodiments, the hydrophilic polymer block is maleic anhydride copolymer. In some embodiments, the hydrophilic polymer block is poly(2-methyloxazoline).

In various embodiments, the ratio of two copolymers in the hydrophilic polymer block is 20:80, 25:75, 30:70, 35:65, 40:60, 45:55, 50:50, 55:45, 60:40, 65:35, 70:30, 75:25, 80:20, 85:15 or any ratio in between. In some embodiments, the ratio of two copolymers in the hydrophilic polymer block is 20:80 to 80:20. In some embodiments, the ratio of two copolymers in the hydrophilic polymer block is 30:70 to 70:30. In some embodiments, the ratio of two copolymers in the hydrophilic polymer block is 40:60 to 60:40. In some embodiments, the ratio of two copolymers in the hydrophilic polymer block is 50:50 to 85:15.

In some embodiments, the hydrophilic polymer block further comprises a primary reactive chemical group. In some embodiments, the hydrophilic polymer block is terminally end capped with a primary reactive chemical group and the other terminus is covalently attached to either a hydrophobic polymer block or another hydrophilic polymer block. In some embodiments, the primary reactive chemical group is an amine moiety, a carboxylic acid moiety, an activated carboxylic acid moiety, an alcohol moiety, a halide moiety, a maleimide moiety, an azide moiety, an alkene, an alkyne, or a thiol moiety. In some embodiments, the primary reactive chemical group is reacted with to form a linker with a secondary reactive chemical group. In some embodiments, the secondary reactive chemical group is an amine moiety, a carboxylic acid moiety, an activated carboxylic acid moiety, an alcohol moiety, a halide moiety, a maleimide moiety, an azide moiety, or a thiol moiety. In some embodiments, the primary reactive chemical group is used to directly attach a biosensor molecule to the polymersome. In other embodiments, the secondary reactive group is used to attach a biosensor molecule to the polymersome.

In some embodiments, the primary reactive chemical group is an amine moiety. In further embodiments, the amine moiety is further thiolated with 2-iminothiolane (2-IT). In still further embodiments, the thiol product of the reaction between the amine moiety and 2-IT is further reacted with a derivatized antibody. In some embodiments, the derivatized antibody reacts with a thiol moiety on the polymersome. In some embodiments, the derivatized antibody is an SMCC-derivatized CD4-monoclonal antibody. In some embodiments, the derivatized antibody is an SPDP-derivatized CD4 monoclonal antibody.

In some embodiments, the hydrophilic polymer block is attached to a biosensor molecule. It is envisioned that the biosensor molecule can be, but is not limited to, a dye, fluorescence protein, nanomaterial (e.g., Quantum Dot), chemiluminescence-generating molecule, a conjugate between dye and chemiluminescence-generating molecule, a conjugate between fluorescence protein and chemiluminescence-generating molecule, a conjugate between a nanomaterial (e.g., Quantum Dot) and chemiluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium or conjugate of any two of the items described above. In some embodiments, the biosensor molecule is a protein, peptide, affinity ligand, antibody, antibody fragment, sugar, lipid, nucleic acid or an aptamer. In some embodiments, the biosensor molecule is a substrate for an enzyme, a substrate analog for an enzyme, a ligand, or a ligand analog for a receptor. In some embodiments, the biosensor molecule is a DNA aptamer, a RNA aptamer, a modified nucleic aptamer, or a peptide aptamer. In some embodiments, the biosensor molecule is avidin. In some embodiments, the biosensor molecule is streptavidin. In some embodiments, the biosensor molecule is an antigen-specific antibody.

In some embodiments, the polymersome comprises an acceptor dye. In some embodiments, the acceptor dye is conjugated to the biosensor molecule. In some embodiments, the acceptor dye is encapsulated by the polymersome. In some embodiments, the acceptor dye is conjugated to the hydrophilic polymer block. It is envisioned that the acceptor dye can be, but is not limited to, rhodamine, coumarin, cyanine, xanthene, polymethine, pyrene, dipyrromethene borondifluoride, napthalimide, a phycobiliprotein, peridinium chlorophyll proteins, conjugates thereof, and combinations thereof. Non-limiting examples of acceptor dyes include, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 630/650, BODIPY® 650/665, BODIPY® R6G, BODIPY® TMR, BODIPY® TR, conjugates thereof, and combinations thereof.

In further embodiments, the acceptor dye contains a signaling chromophore for resonant energy transfer (Forster (or fluorescence) resonance energy transfer, FRET). Exemplary chromophores include, but are not limited to, 2,1,3-benzothiadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, Nile Red, Coumarin 6, tetraphenylporphyrin, cyanine dyes (e.g., 1,1'-dioctadecyl-3,3,3',3'-tetramethylindodicarbocyanine and 1,1'-dioctadecyl-3,3,3',3'-tetramethylindotricarbocyanine), olefins, and cyano-substituted olefins and isomers thereof.

Hydrophobic Fluorescent Polymers

In some embodiments, the aqueous soluble polymersomes comprise one or more hydrophobic fluorescent polymers and a plurality of amphiphilic copolymers encapsulating the fluorescent polyfluorene polymer. The hydrophobic fluorescent polymer is an intensely fluorescent molecule. In some embodiments, the hydrophobic fluorescent polymer is a polyfluorene polymer, polyfluorene copolymer, or fluorescent homopolymer. In various embodiments, the hydrophobic fluorescent polymer has a number average molecular weight of about 5000, 10000, 15000, 20000, 25000, or 30000 Daltons, including increments therein. In some embodiments, the hydrophobic fluorescent polymer has a number average molecular weight of about 5,000 to about 10,000 Daltons. In some embodiments, the hydrophobic fluorescent polymer has a number average molecular weight of about 5,000 to about 15,000 Daltons. In some embodiments, the hydrophobic fluorescent polymer has a number average molecular weight of about 5,000 to about 20,000 Daltons. In some embodiments, the hydrophobic fluorescent polymer has a number average molecular weight of about 5,000 to about 30,000 Daltons. In some embodiments, the hydrophobic fluorescent polymer has a number average molecular weight of about 10,000 to about 15,000 Daltons. In some embodiments, the hydrophobic fluorescent polymer has a number average molecular weight of about 10,000 to about 20,000 Daltons. In some embodiments, the hydrophobic fluorescent polymer has a number average molecular weight of about 10,000 to about 30,000 Daltons. In some embodiments, the hydrophobic fluorescent polymer has a number average molecular weight of about 20,000 to about 30,000 Daltons.

In some embodiments, the hydrophobic fluorescent polymer is selected from the optionally substituted polymer group consisting of poly(fluorene), poly(fluorene-alt-benzothiadiazole), poly(fluorene-alt-benzooxadiazole), poly(fluorene-alt-thiophene), and poly(fluorene-alt-phenylene). The polyfluorene polymer, polyfluorene copolymer, or fluorescent homopolymer may be optionally substituted poly(fluorene-alt-benzothiadiazole).

Polyfluorene polymers, polyfluorene copolymers, and fluorescent homopolymers may include, but are not limited to, poly[(9,9-dioctyl-2,7-divinylenefluorenylene)-alt-co (9,10-anthracene)]; poly[(9,9-dioctyl-2,7-divinylenefluorenylene)-alt-co-{2-methoxy-5-(2-ethylhexyloxy)-1,4-phenylene}]; poly[(9,9-dioctyl-2,7-divinylenefluorenylene)-alt-co-(1,4-phenylene)]; poly[(9,9-dioctylfluorenyl-2,7-diyl)-alt-co-(1,4-benzo-{2,1',3}-thiadiazole)]; poly[(9,9-dihexylfluorenyl-2,7-diyl)-alt-co-(2-methoxy-5-{2-ethylhexyloxy}-1,4-phenylene)]; poly[(9,9-dioctylfluorenyl-2,7-diyl)-co-(2,5-p-xylene)]; poly[(9,9-dioctylfluorenyl-2,7-diyl)-co-(N,N'-diphenyl)-N,N'-di(p-butylphenyl)-1,4-diamino-benzene)]; poly[(9,9-dioctylfluorenyl-2,7-diyl)-co-(1,4-benzo-{2,1',3}-thiadiazole)]; poly[2-methoxy-5-(2-ethylhexyloxy)-1,4-phenylene-vinylene], optionally end capped with dimethylphenyl; poly[2-methoxy-5-(2-ethylhexyloxy)-1,4-phenylene-vinylene], optionally end capped with polysilsesquioxane; poly[2-methoxy-5-(3,7-dimethyloctyloxy)-1,4-phenylene-vinylene], optionally end capped with dimethylphenyl; poly[2-methoxy-5-(3,7-dimethyloctyloxy)-1,4-phenylene-vinylene], optionally end capped with polysilsesquioxane; poly[9,9-dioctylfluorenyl-2,7-diyl], optionally end capped with dimethylphenyl; poly[9,9-dioctylfluorenyl-2,7-diyl], optionally end capped with polysilsesquioxane; poly[9,9-dioctylfluorenyl-2,7-diyl], optionally end capped with N,N-bis(4-methylphenyl)-aniline; poly[9,9-dioctylfluorenyl-2,7-diyl], optionally end capped with 2,5-diphenyl-1,2,4-oxadiazole; poly[9,9-di-(2-ethylhexyl)-fluorenyl-2,7-diyl], optionally end capped with dimethylphenyl; poly[9,9-di-(2-ethylhexyl)-fluorenyl-2,7-diyl], optionally end capped with polysilsesquioxane; poly[9,9-di-(2-ethylhexyl)-fluorenyl-2,7-diyl], optionally end capped with N,N-bis(4-methylphenyl)-aniline; poly[9,9-di-(2-ethylhexyl)-fluorenyl-2,7-diyl], optionally end capped with 2,5-diphenyl-1,2,4-oxadiazole; poly[2-(5-cyano-5-methylhexyloxy)-1,4-phenylene], optionally end capped with dimethylphenyl; and poly[2,5-dioctyl-1,4-phenylene], optionally end capped with dimethylphenyl; poly[9,9-di(3,3'-N,N'-trimethyl-ammonium)propylfluorenyl-2,7-diyl]-alt-(9,9-dioctylfluorenyl-2,7-diyl)] diiodide salt, optionally end capped with dimethylphenyl; poly[2,5-bis(3,7-dimethyloctyloxy)-1,4-phenylene-vinylene]; poly(9,9-di{2-[2-(2-methoxy-ethoxy)ethoxy]ethyl}fluorenyl-2,7-diyl), optionally end capped with dimethylphenyl; and poly-BODIPY fluorescent polymers.

Polyfluorene polymers, polyfluorene copolymers, and fluorescent homopolymers may include, but are not limited to, ADS106RE, ADS108GE, ADS128GE, ADS133YE, ADS136BE, ADS145UV, ADS180BE, ADS232GE, ADS233YE, ADS100RE, ADS200RE, ADS104RE, ADS204RE, ADS300RE, ADS129BE, ADS229BE, ADS329BE, ADS429BE, ADS131BE, ADS231BE, ADS331BE, ADS431BE, ADS160BE, ADS120BE, and ADS121BE, which are commercially available from American Dye Sources.

In some embodiments, the aqueous soluble polymersome encapsulates at least two hydrophobic fluorescent polymers, at least one of which acts as a light harvesting polymer and at least one of which acts as a signaling chromophore in a FRET process. Signaling chromophores can include, but are not limited to, 2,1,3-benzothiadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, Nile Red, Coumarin 6, tetraphenylporphyrin, cyanine dyes (e.g., 1,1'-dioctadecyl-3,3,3',3'-tetramethylindodicarbocyanine and 1,1'-dioctadecyl-3,3,3',3'-tetramethylindotricarbocyanine), olefins, and cyano-substituted olefins and isomers thereof.

Antioxidants

Molecular oxygen is involved in a number of processes which may lead to photodegradation of organic dyes, including formation of singlet oxygen, peroxides, and other reactive oxygen species (ROS). Triplet quenchers and ROS scavengers are often added as antifade agents, to reduce the rate of photobleaching in fluorescence microscopy of biological samples. For the application of polyfluorene nanoparticles (PFNs) in fluorescence-based applications, such as flow cytometric analysis and imaging, photobleaching involving oxygen is expected to be a critical problem. The photostability of PFNs can be enhanced by incorporating hydrophobic antifade agents in PFNs during nanoparticle formation.

In some embodiments, the aqueous soluble polymersomes encapsulate one or more hydrophobic fluorescent polymers and one or more antioxidants. In some embodiments, the aqueous soluble polymersomes encapsulate one or more polyfluorene polymers, polyfluorene copolymers, or fluorescent homopolymers and one or more antioxidants. In some embodiments, the one or more antioxidants improve the photostability of the polymersomes.

In some embodiments, the antioxidants may be antifade or triple-state quencher (TSQ) compounds. Antifade and TSQ compounds include, but are not limited to, butylated hydroxytoluene (BHT), 3-(3,5-ditert-butyl-4-hydroxyphenyl) propionic acid stearyl ester (PASE), triphenylamine (TPA), trans-stilbene (TSB), cyclooctatetraene (Cot), 4-nitrobenzyl alcohol (NBA), and 6-hydroxy-2,5,7,8-tetramethylchroman-2-carboxylic acid (Trolox).

Preparation of Polymersomes

The amphiphilic multiblock copolymers that self-assemble into the enclosure structure of the polymersomes disclosed herein are prepared by covalent attachment of the individual blocks. In some embodiments, the hydrophobic polymer block precursor is terminated with a reactive chemical group which can react with a bifunctional hydrophilic polymer block precursor. This bifunctional hydrophilic polymer block precursor comprises two reactive chemical groups on either end of the precursor, one of which can react with the hydrophobic polymer block precursor or another bifunctional hydrophilic polymer block precursor and the other reactive group can optionally be tethered to a biosensor molecule after polymersome formation. The reactive chemical group can be, but is not limited to, an amine moiety, a carboxylic acid moiety, an activated carboxylic acid moiety, an alcohol moiety, a halide moiety, a maleimide moiety, an azide moiety, an alkene, an alkyne, or a thiol moiety. In some embodiments, the two reactive chemical groups of the bifunctional hydrophilic polymer block are identical. In some embodiments, the two reactive chemical groups of the bifunctional hydrophilic polymer block are different. A non-limiting example of an amphiphilic diblock polymer prepared in this manner is illustrated in FIG. 1.

In some embodiments, postpolymerization dispersions of a plurality of the amphiphilic multiblock copolymers leads to the formation of aqueous soluble polymersomes described herein. In some embodiments, postpolymerization dispersions of a plurality of the amphiphilic multiblock copolymers through a precipitation technique lead to the formation of aqueous soluble polymersomes. In other embodiments, postpolymerization dispersions of a plurality of the amphiphilic multiblock copolymers through an emulsion technique lead to the formation of aqueous soluble polymersomes.

In some embodiments, when a plurality of amphiphilic multiblock copolymers and one or more hydrophobic fluorescent polymers are agitated together in water, aqueous soluble polymersomes that encapsulate the one or more hydrophobic fluorescent polymers are formed. In further embodiments, the amphiphilic multiblock copolymers are diblock copolymers.

In some embodiments, when a plurality of amphiphilic multiblock copolymers, one or more hydrophobic fluorescent polymers, and one or more antioxidants are agitated together in water, aqueous soluble polymersomes that encapsulate the one or more hydrophobic fluorescent polymers and the one or more antioxidants are formed. In further embodiments, the amphiphilic multiblock copolymers are diblock copolymers.

In some embodiments, the fluorescent aqueous soluble polymersomes are further derivatized through the remaining reactive chemical groups on the terminal ends of the hydrophilic polymer blocks, these reactive chemical groups being localized on the surface of the polymersome. In some embodiments, the fluorescent aqueous soluble polymersomes are attached to biosensor molecules. In further embodiments, the biosensor molecules are antigen-specific antibodies. A non-limiting example of this antibody-polymersome conjugate is shown in FIG. 9.

In one aspect, disclosed herein are methods of preparing an aqueous soluble polymersome comprising one or more hydrophobic fluorescent polymers, the method comprising: (a) forming a plurality of amphiphilic copolymers each comprising a hydrophobic block and a hydrophilic block; (b) adding one or more hydrophobic fluorescent polymers to the plurality of amphiphilic copolymers; and (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of the polymersome that is oriented toward an aqueous phase. In some embodiments, the amphiphilic copolymers are diblock copolymers. In some embodiments, the hydrophobic block of plurality of amphiphilic copolymers is PLGA. In some embodiments, the hydrophilic block of plurality of amphiphilic copolymers is PEG. In some embodiments, the formation of the amphiphilic copolymers comprises reacting PLGA with bis-aminopropyl-PEG in the presence of carbodiimide. In some embodiments, in step (c), the mixture and aqueous system is agitated. In some embodiments, the method further comprises filtering the polymersomes in the aqueous system. In some embodiments, the method further comprises concentrating the polymersomes in the aqueous system. In some embodiments, the method further comprises reacting the polymersomes with a thiolating reagent. In some embodiments, the method further comprises attaching an antigen-specific antibody to the polymersomes.

Uses of Polymersomes

Due to their low water-solubility, hydrophilic fluorescent polymers are not amenable for use in aqueous systems. However, encapsulation in aqueous soluble polymersomes enables the use of hydrophobic fluorescent polymers in water-containing media.

In one aspect, disclosed herein are methods of solubilizing one or more hydrophobic fluorescent polymers, the method comprising (a) forming a plurality of amphiphilic copolymers each comprising a hydrophobic block and a hydrophilic block; (b) adding one or more hydrophobic fluorescent polymers to the plurality of amphiphilic copolymers; and (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of the polymersome that is oriented toward an aqueous phase. In some embodiments, the amphiphilic copolymers are diblock copolymers.

In some embodiments, biosensor molecules, such as antigen-specific antibodies, are linked to the functionalizable chemical groups, e.g., amine moieties, on the surface of the polymersomes. These fluorescent biosensor-polymersome conjugates can be used in a number of applications, including, but not limited to, cell staining as well as analyte detection in cell-free assay environments. In some embodiments, the fluorescent biosensor-polymersome conjugates are used in flow cytometry applications.

Disclosed herein are assay methods for detecting a target biomolecule in a sample. In one aspect, an assay method for detecting a target biomolecule in a sample comprises (a) providing a sample that is suspected of containing a target biomolecule; (b) providing an aqueous soluble polymersome disclosed herein that is conjugated to a sensor biomolecule, wherein the sensor biomolecule is capable of interacting with the target biomolecule or a target-associated biomolecule and wherein the polymersome optionally comprises an acceptor dye; (c) contacting the sample with the sensor biomolecule and the aqueous soluble polymersome in a solution under conditions in which the sensor biomolecule can bind to the target biomolecule or a target-associated biomolecule if present; and (d) applying a light source to the sample that can excite the fluorescent polyfluorene polymer in the polymersome, and detecting whether light is emitted from the polymersome. In some embodiments, the sensor biomolecule is a protein, peptide, affinity ligand, antibody, antibody fragment, sugar, lipid, nucleic acid or an aptamer. In some embodiments, the sensor biomolecule is an antibody. In some embodiments, the target biomolecule is a target protein expressed on a cell surface. In some embodiments, the method is configured for flow cytometry, intracellular staining, immunohistochemistry or FISH.

EXAMPLES

Example 1

Figure 2:
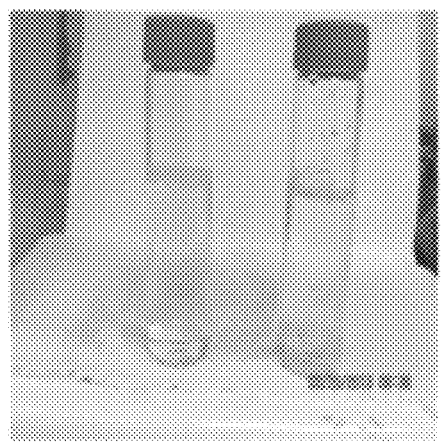
FIG. 2 illustrates a visual comparison of the polyfluorenebenzothiadiazole-encapsulated polymersomes of FIG. 1 in water with polyfluorenebenzothiadiazole in water.
Figure 3:
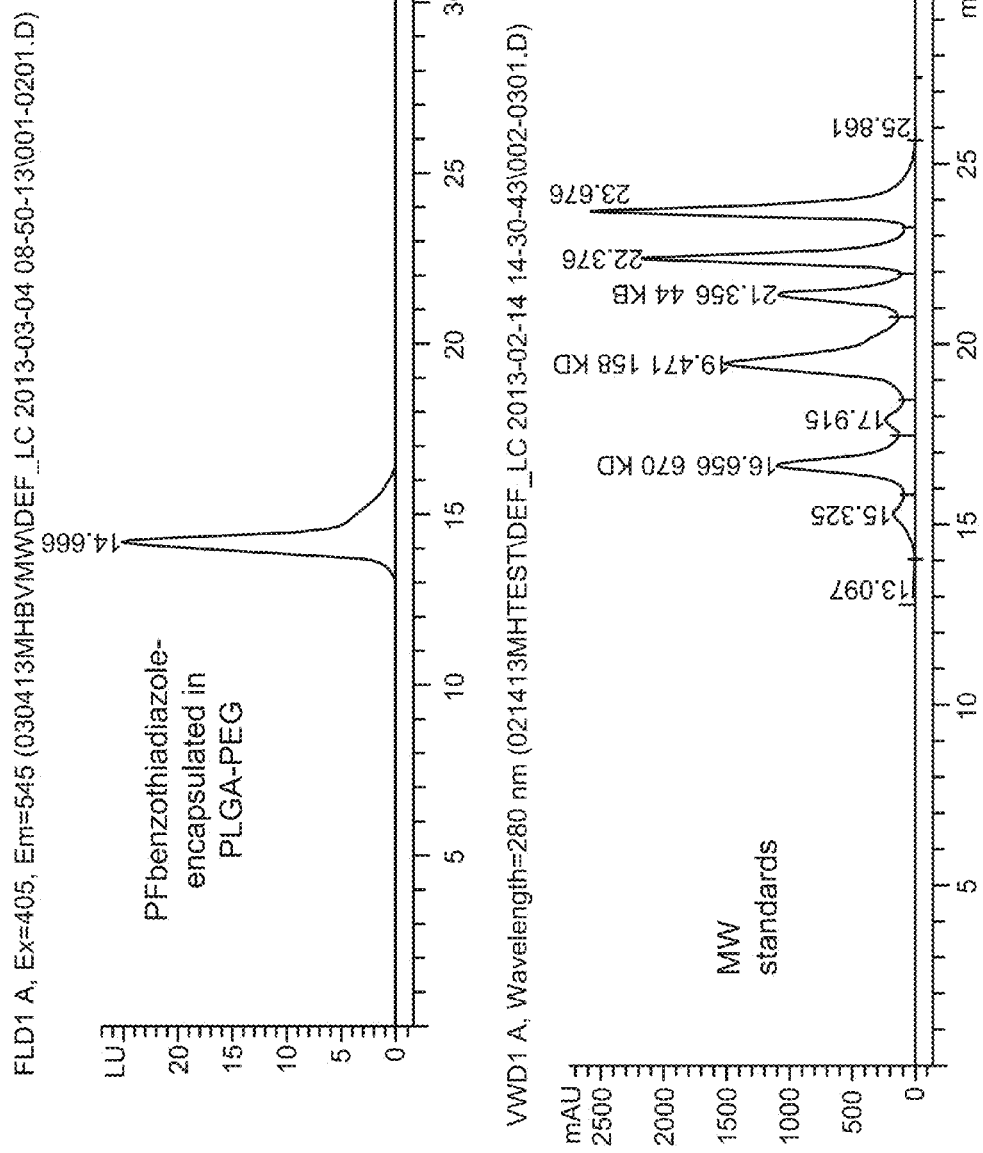
FIG. 3 illustrates the size exclusion chromatography data for the polyfluorenebenzothiadiazole-encapsulated polymersomes of FIG. 1 compared with molecular weight standards.

Preparation of Aqueous Soluble Polymersomes using $PLGA_{5000}$-$PEG_{2000}$-$NH_2$ Encapsulating Polyfluorenebenzothiadiazole The diblock copolymer of $PLGA_{5000}$-$PEG_{2000}$-$NH_2$ was prepared by attachment of a low molecular weight PLGA of about 5000 Dalton to bis-aminopropyl-PEG ($H_2N$-PEG-$NH_2$) of average molecular weight of about 2000 Dalton (FIG. 1). The desired amide formation between the terminal carboxylic acid of the PLGA with one of the amine moieties of bis-aminopropyl-PEG was performed under carbodiimide/dichloromethane conditions. This resultant diblock polymer was used as the amphiphilic carrier polymer to facilitate the encapsulation of polyfluorenebenzothia-diazole (MW=10,000-20,000 Da; Ex (max)=454 nm; Em=545 nm; Sigma-Aldrich) into water-soluble polymersomes of core/shell structure. The formation of polyfluorenebenzothiadiazole-encapsulated polymersomes was performed using a precipitation technique in which the amphiphilic diblock polymer (60 mg, 15 μmol) and polyfluorenebenzo-thiadiazole (440 μg, 30 nmol) were mixed vigorously under aqueous conditions. The resulting colloidal suspension (120 ml) was filtered, and solvent was removed until the desired concentration was obtained. As demonstrated in FIG. 2, polyfluorenebenzothiadiazole is insoluble in water, visible to the naked eye as clumps of material, but appears to be "dissolved" in the aqueous system once encapsulated in the aqueous soluble PLGA-PEG-$NH_2$ polymersome. Size exclusion chromatography of these polyfluorenebenzothiadiazole-encapsulated polymersomes is shown in FIG. 3.

Notably, attempts to use a larger molecular weight PLGA of 46000 Dalton indicated that the encapsulation of polyfluorenebenzothiadiazole was not possible with the resultant PLGA-PEG copolymer using this precipitation technique.

Example 2

Figure 4:
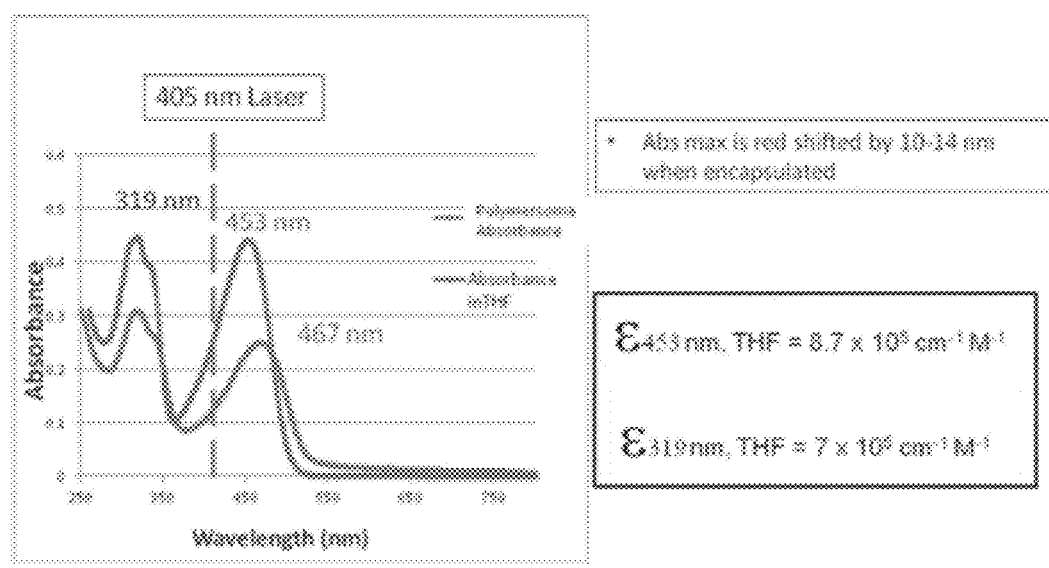
FIG. 4 illustrates a comparison of the absorption properties of the polyfluorenebenzothiadiazole-encapsulated polymersomes of FIG. 1 in buffer and the absorption properties of polyfluorenebenzothiadiazole in tetrahydrofuran.
Figure 5:
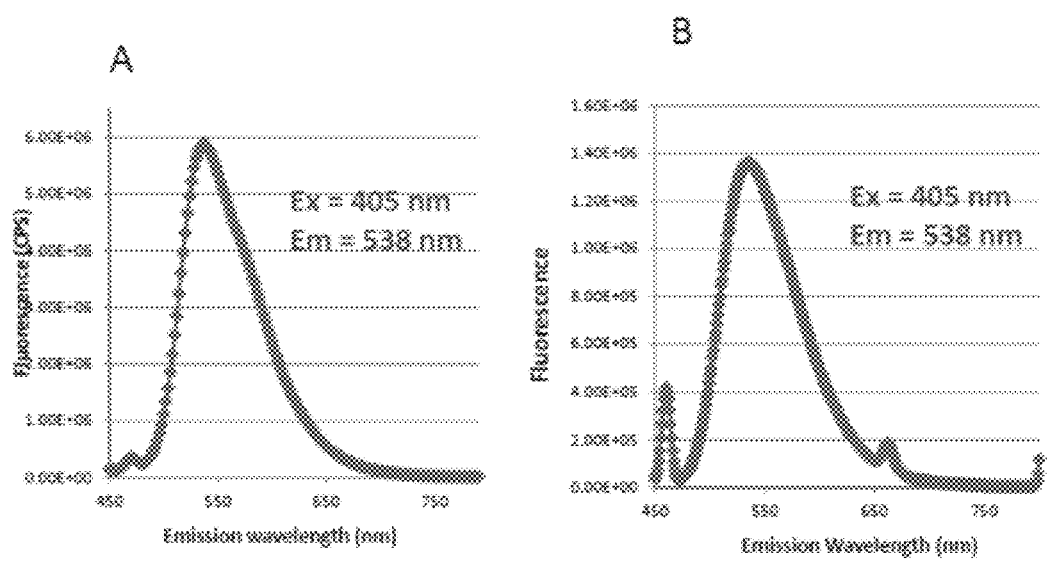
FIG. 5 illustrates a comparison of the fluorescence emission properties of the polyfluorene-benzothiadiazole-encapsulated polymersomes of FIG. 1 in buffer and the fluorescence emission properties of polyfluorenebenzothiadiazole in tetrahydrofuran.

Characterization of Aqueous Soluble Polymersomes using PLGA$_{5000}$-PEG$_{2000}$-NH$_2$ Encapsulating Polyfluorenebenzothiadiazole Comparison with Polyfluorene in Organic Solvent The polymersomes of Example 1 demonstrated absorption properties slightly different from those of polyfluorenebenzothiadiazole in organic solvent (FIG. 4). The absorption of the encapsulated polyfluorenebenzothiadiazole was about 10-14 nm red-shifted compared to that of polyfluorenebenzothiadiazole in an organic solvent, tetrahydrofuran (THF). Also, the ratio of two absorption peaks, 319 and 467 nm, was smaller than those of polyfluorenebenzothiadiazole in organic solvent that approaches unity. These spectral differences suggest that the microenvironment of the encapsulated polyfluorenebenzothiadiazole in the core of the polymersomes is different from that of solvated polyfluorenebenzothiadiazole in organic solvent. However, the fluorescence emission of the encapsulated polyfluorenebenzothiadiazole has virtually identical spectral properties to that of polyfluorenebenzothiadiazole dissolved in organic solvent (FIG. 5). Thus, encapsulation does not adversely impact the fluorescence emission of the encapsulated polyfluorenebenzothiadiazole in the core of the polymersomes.

Quantitation of Hydrophobic Fluorescent Polymer Molecules in Polymersome.

Figure 6:
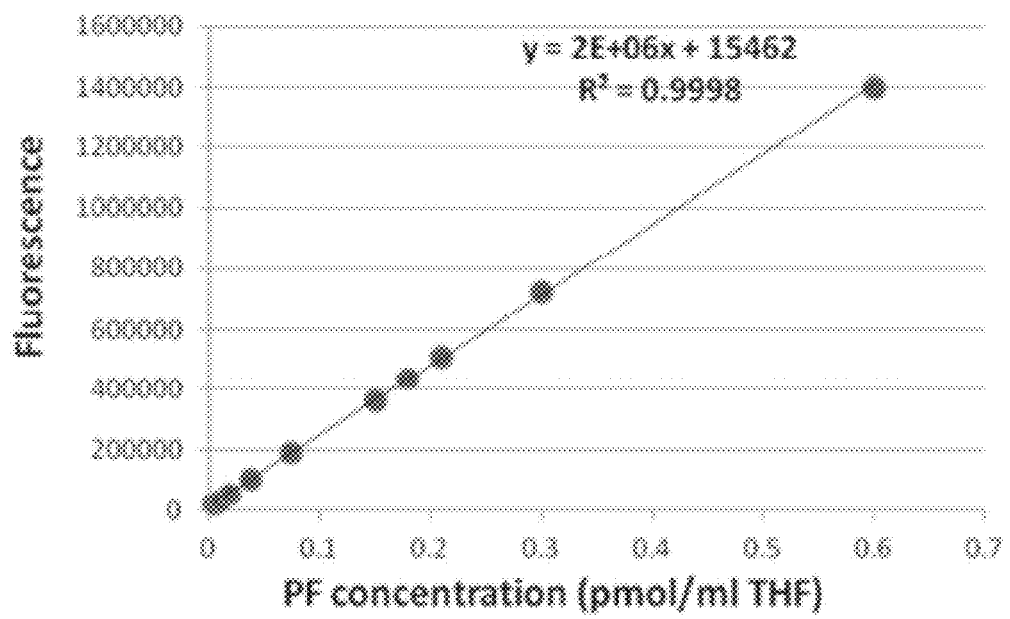
FIG. 6 illustrates a standard curve for quantitation of MESF for polyfluorenebenzothiadiazole.

Due to the partial quenching of the fluorescent polymer in the polymersome, quantitation of the total number of fluorochrome is not of significant value. However, the number of Molecules of Equivalent Soluble Fluorochrome (MESF) is more useful and can be obtained for any suspension of polymersomes, including antibody-polymersome conjugates. A standard curve for quantitation of MESF was obtained for the polyfluorenebenzothiadiazole (FIG. 6). Based on this curve, it was determined that 1.25 pmol fluorophore/µL of encapsulated polymersomes translated to $7.5 \times 10^{11}$ MESF/µL of encapsulated polymersome suspension.

Example 3

Figure 7:
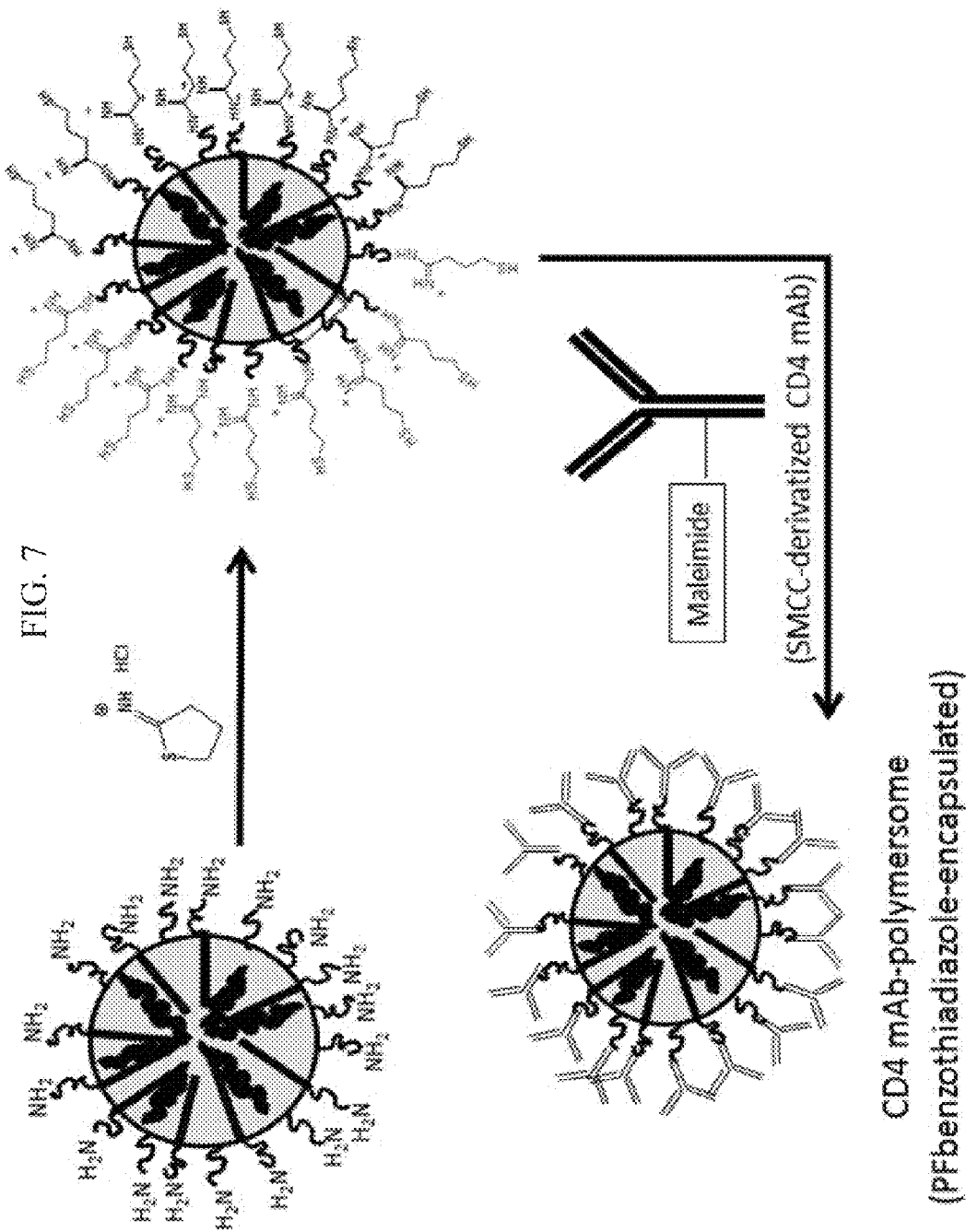
FIG. 7 illustrates the general scheme for the preparation of a non-limiting example of antibody-polymersome conjugates; in this case, the polyfluorenebenzothiadiazole-encapsulated polymersomes of FIG. 1 were conjugated to an SMCC-derivatized CD4 monoclonal antibody.
Figure 8:
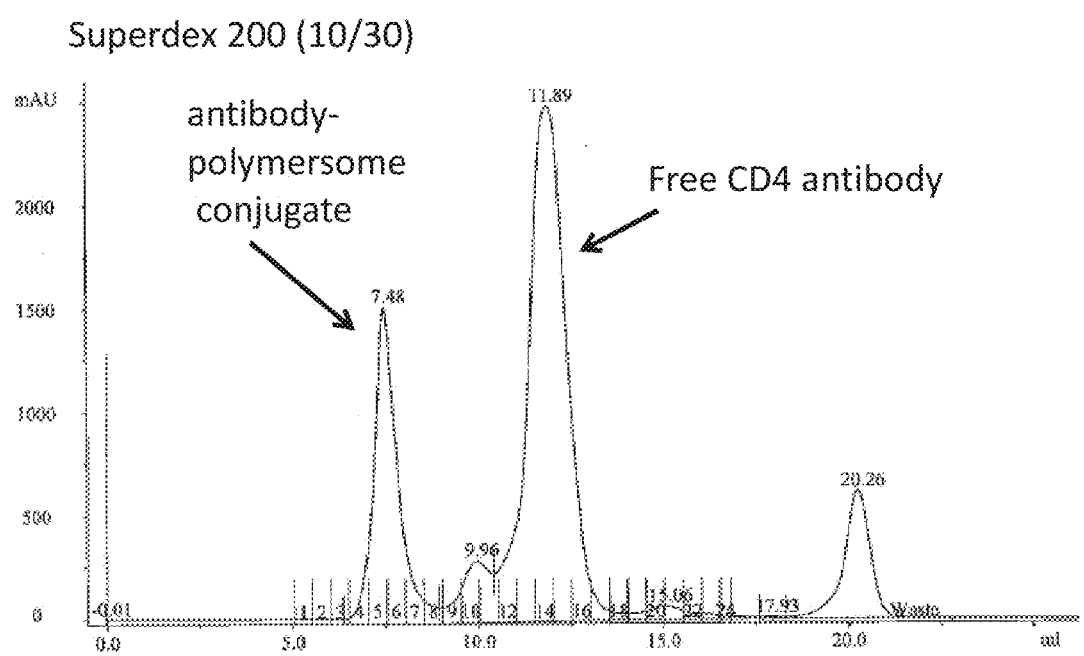
FIG. 8 illustrates the size exclusion chromatography data for the fluorescent antibody-polymersome conjugates of FIG. 7.

Preparation of Aqueous Soluble Antibody-Polymersome Conjugates using Polymersomes of PLGA$_{5000}$-PEG$_{2000}$-NH$_2$ Encapsulating Polyfluorenebenzothiadiazole The general scheme for conjugation of antibodies to the surface of the polyfluorene-benzothiadiazole-encapsulated polymersomes of Example 1 is shown in FIG. 7. Amine functional groups from the PEG moiety on the surface of the particles were modified with Traut's reagent (2-Iminithiolane; 2-IT). The resulting free sulfhydryl groups were conjugated to an SMCC-derivatized antibody (anti-CD4) carrying reactive maleimide groups. Size exclusion chromatography for the purification of this antibody-polymersome conjugate is shown in FIG. 8.

Example 4

Characterization of Aqueous Soluble Antibody-Polymersome Conjugates

The CD4 antibody-polymersome conjugates of Example 3 were further evaluated for the presence of the antibody on the nanoparticles. FIG. 9 illustrates the flow cytometric analysis of the fluorescent antibody-polymersome conjugates after being captured on anti-kappa beads. The beads were coated with anti-kappa antibodies that capture the kappa light chain of CD4 antibodies present on the antibody-polymersome conjugates. The experimental results clearly indicated that the captured antibody-polymersome conjugated on the beads were fluorescent (histogram #4) and that their fluorescent signal was sufficiently high enough to separate them from the non-specific background signal (histograms #1 and 3). As a positive control, BV510-CD4 conjugates (conjugates between CD4 antibody and BRILLIANT VIOLET™ 510 from BD Biosciences) were captured on the same beads (histogram #2).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of preparing an aqueous soluble polymersome comprising one or more hydrophobic fluorescent polymers, the method comprising
   (a) forming a plurality of amphiphilic diblock copolymers each comprising a hydrophobic block and a hydrophilic block;
   (b) adding one or more hydrophobic fluorescent polymers to the plurality of amphiphilic copolymers; and
   (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of the polymersome that is oriented toward an aqueous phase;
      wherein the hydrophobic block of the amphiphilic diblock copolymer is poly(lactide-co-glycolic acid) (PLGA); and
      the hydrophilic block of the amphiphilic diblock copolymer is selected from a hydrophilic polysaccharide, a polyether, polymethacrylate, poly(methacrylic acid), polyacrylic acid, polyacrylate, poly(alkylacrylic acid), poly(alkylacrylate), polyacrylamide, poly(N-isopropylacrylamide), poly(2-ethyl-2-oxazoline), poly(vinyl alcohol), poly(vinyl acid), poly(2-methyloxazoline) and copolymer combinations thereof.

2. The method of claim 1, wherein the hydrophilic block of the amphiphilic diblock copolymers is PEG.

3. The method of claim 1, wherein in step (c), the mixture and aqueous system is agitated.

4. The method of claim 1, wherein the method further comprises filtering the polymersomes in the aqueous system.

5. The method of claim 1, wherein the method further comprises concentrating the polymersomes in the aqueous system.

6. The method of claim 1, wherein the method further comprises reacting the polymersomes with a thiolating reagent.

7. A method of solubilizing one or more hydrophobic fluorescent polymers, the method comprising (a) reacting PLGA with bis-aminopropyl-PEG in the presence of carbodiimide thereby forming a plurality of amphiphilic diblock copolymers each comprising a PLGA hydrophobic block having an average molecular weight of about 2,000 to 20,000 Daltons and a hydrophilic block that is PEG;

(b) adding one or more hydrophobic fluorescent polymers to the plurality of amphiphilic copolymers; and (c) placing the mixture of step (b) into an aqueous system so that the plurality of amphiphilic copolymers encapsulate the one or more hydrophobic fluorescent polymers, wherein the hydrophobic block forms a hydrophobic core structure and a hydrophilic block is oriented on the surface of a polymersome that is oriented toward an aqueous phase.

8. The method of claim 7, wherein the PLGA hydrophobic block has a number average molecular weight of about 5,000 Daltons and the PEG hydrophilic block has a number average molecular weight of about 2,000 Daltons.

9. An assay method for detecting a target biomolecule in a sample comprising:

(a) providing a sample that is suspected of containing a target biomolecule;

(b) providing an aqueous soluble polymersome of claim 1 that is conjugated to a sensor biomolecule, wherein the sensor biomolecule is capable of interacting with the target biomolecule or a target-associated biomolecule and wherein the polymersome optionally comprises an acceptor dye;

(c) contacting the sample with the sensor biomolecule and the aqueous soluble polymersome in a solution under conditions in which the sensor biomolecule can bind to the target biomolecule or a target-associated biomolecule if present; and (d) applying a light source to the sample that can excite the fluorescent polyfluorene polymer in the polymersome, and detecting whether light is emitted from the polymersome.

10. The assay method of claim 9, wherein the sensor biomolecule is a protein, peptide, affinity ligand, antibody, antibody fragment, sugar, lipid, nucleic acid or an aptamer.

11. The assay method of claim 9, wherein the sensor biomolecule is an antibody.

12. The assay method of claim 9, wherein the target biomolecule is a target protein expressed on a cell surface.

13. The assay method of claim 9, wherein the method is configured for flow cytometry, intracellular staining, immunohistochemistry or FISH.

14. The method of claim 7, wherein the method further comprises attaching an antigen-specific antibody to the polymersomes.

15. The method of claim 7, wherein the one or more hydrophobic fluorescent polymers are polyfluorene polymers or polyfluorene copolymers.

16. The method of claim 7, wherein the one or more hydrophobic fluorescent polymers are polyfluorene polymers or polyfluorene copolymers.

17. The method of claim 7, wherein in step (c), the mixture and aqueous system is agitated.

18. The method of claim 7, wherein the method further comprises filtering the polymersomes in the aqueous system.

19. The method of claim 7, wherein the method further comprises concentrating the polymersomes in the aqueous system.

20. The method of claim 7, wherein the method further comprises reacting the polymersomes with a thiolating reagent.

21. The method of claim 7, wherein the method further comprises attaching an antigen-specific antibody to the polymersomes.

* * * * *